US008221680B1

(12) United States Patent
Thomas

(10) Patent No.: US 8,221,680 B1
(45) Date of Patent: Jul. 17, 2012

(54) STERILIZING HANDLE FOR A CULINARY TOOL APPARATUS AND METHOD

(76) Inventor: Beverly A. Thomas, Lakeland, FL (US)

( * ) Notice: Subject to any disclaimer, the term of this patent is extended or adjusted under 35 U.S.C. 154(b) by 268 days.

(21) Appl. No.: 12/387,586

(22) Filed: May 6, 2009

(51) Int. Cl.
*A61L 2/00* (2006.01)
*B26B 5/00* (2006.01)

(52) U.S. Cl. .......................................... 422/28; 30/157

(58) Field of Classification Search .................. 30/157; 422/28

See application file for complete search history.

(56) References Cited

U.S. PATENT DOCUMENTS

| 1,491,780 | A | 4/1924 | Abbott |
| 4,832,942 | A | 5/1989 | Crace |
| 4,856,140 | A | 8/1989 | Visco et al. |
| 6,298,521 | B1 | 10/2001 | Butterfield |
| 7,204,957 | B2 | 4/2007 | Tozer |
| 7,597,223 | B1* | 10/2009 | Martinez ....................... 224/197 |
| 2005/0026802 | A1* | 2/2005 | Kilkenny et al. ............. 510/295 |

* cited by examiner

*Primary Examiner* — Kevin Joyner
(74) *Attorney, Agent, or Firm* — William M. Hobby, III

(57) ABSTRACT

A culinary tool having a sterilizing handle apparatus and method includes a culinary tool, such as a fork, spoon or tongs, which has a tang extending therefrom. A handle is removably attached to the culinary tool over the culinary tool tang which handle includes a non-porous sleeve having a disinfectant impregnated foam reservoir therearound encapsulated in a semipermeable layer. Pressure applied to the handle causes a disinfectant material to ooze through the semipermeable layer to disinfect the handle.

11 Claims, 2 Drawing Sheets

STERILIZING HANDLE FOR A CULINARY TOOL APPARATUS AND METHOD

BACKGROUND OF THE INVENTION

The present invention relates to a culinary tool, such as a fork, knife or spoon, and especially to a culinary tool handle which is maintained in a sterile condition when used by multiple users.

In the past, it has been common for salad bars in public restaurants to have various tools, such as salad tongs, forks, spoons and the like, to have placed by the salad bar for the public to use in making a salad. A restaurant patron may use salad tongs to grab various types of salad greens, such as lettuce or spinach, for deposit on a salad plate and then use a fork for selecting other items and a spoon for the salad dressing. These culinary tools are handled by a large number of patrons at the restaurant and are prone to picking up germs and microbiological agents and the like from each of the patrons making a salad. This easily allows common as well as infectious bacteria to pass from one person to another as patrons proceed through a salad bar line. It thereby becomes advantageous to have culinary tools which are constantly sterilized by the destruction of microbiological agents, such as bacteria, on a continuous basis as each patron uses the culinary tools. It is also important that a disinfectant be used that is not harmful to a patron using the culinary tool and that culinary tools do not have excess disinfectants on the handles. It is also important to have a disinfectant handle which is firmly affixed to the culinary tool and at the same time can be rapidly changed to maintain disinfecting surfaces.

The present invention provides for a rapidly changeable handle for a culinary tool, such as tongs, a fork or a knife, which will maintain the handle in a sterile condition for a long period of time through a large number of users of the tool. It also helps maintains the user's hands in a generally sterile condition so as to avoid the spread of bacteria.

In the prior U.S. Pat. No. 4,856,140 to Visco et al., a sanitary handle cover is provided for fitting over door knobs to separate the user's fingers from coming into contact with the knob and which disinfects the external surface of the knob or handle in order to protect the fingers from contamination.

In the prior U.S. Pat. No. 7,204,957 to Tozer, a sanitizable cushioned sheath for the handle of a culinary knife is used to provide a user with enhanced comfort and support. The handle sheath is molded of a flexible material and is stretched over a conventional handle so that it can be removed and replaced. The handle sheath may also be provided with an internal flushing mechanism for sanitizing the interior of the sheath without requiring it to be removed from the handle.

In the Butterfield U.S. Pat. No. 6,298,521 a door knob sanitizing device is secured on the rear end of a door knob housing on the backing plate behind the door knob. The housing has slots in the front thereof so that disinfectant vapors can reach the door knob.

In the U.S. Pat. No. 4,832,942 to Crace, a disinfectant tape is suitable for mounting on a substrate facility to enable a user to disinfect his or her hands during use of the facility. The tape is enclosed in a liquid-proof cover, such as a shrink sealed package, aluminum or other metal foil, and has a perforate tape cover layer and a central liquid disinfectant containing foam layer along with a double adhesive-backed lower layer and a bottom release liner. The tape is used for door knobs and urinal handles and the like.

The C.P. Abbott U.S. Pat. No. 1,491,780 is for a sanitary handle knob and the like in which the knob has a plurality of holes therein.

The present invention on the other hand is directed towards a culinary tool, such as used at salad bars, and especially to tongs, forks and spoons for which the pubic continuously uses in making a salad at a salad bar and which is used by large number of patrons. The present invention provides for a quickly removable handle for a special culinary tool made to receive the handle which continuous sterilizes the handle during use by the public and which can disinfect the hands of the user at the same time.

SUMMARY OF THE INVENTION

A sterilized handle for a culinary tool includes a culinary tool having a tang extending therefrom and having a handle guard extending generally perpendicular to the tang. The handle is removably attached to the culinary tool and has a generally non-porous hollow sleeve shaped to fit over the tang which has an open end having a flange extending generally perpendicular therefrom and positioned for attaching to the handle guard. The handle sleeve has a disinfectant impregnated foam reservoir therearound encapsulated in a semipermeable membrane. Applying pressure to the culinary tool handle causes disinfectant material to ooze through the semipermeable membrane to disinfect the handle. The handle guard has at least one opening therethrough for cooperating with a movable locking member shaped to fit through the opening in the guard in one position and movable to a second position to latch the handle flange to the guard. The handle guard opening may be of a generally oval shape while the attaching means may be of a generally oval shape and sized to fit through the handle guard opening and rotatable to overlap the edges of the handle guard opening. The handle foam reservoir may be a polystyrene foam saturated with a disinfectant solution, such as alcohol, while the semipermeable membrane may be a cellulose acetate film having a plurality of microscopic openings therein. The culinary tool may be a pair of tongs or a fork or spoon or any other culinary tool.

The process of maintaining a sterile handle for a culinary tool includes the step of selecting a culinary tool and a handle in accordance with the present apparatus, sliding the handle over the selected culinary tool tang and attaching the handle flange to the culinary tool guard so that when pressure is applied to the culinary tool handle, it causes a disinfectant material to ooze through the semipermeable membrane to disinfect the handle.

BRIEF DESCRIPTION OF THE DRAWINGS

Other objects, features, and advantages of the present invention will be apparent from the written description and the drawings in which.

DESCRIPTION OF THE PREFERRED EMBODIMENT

Figures 1, 2, 3:
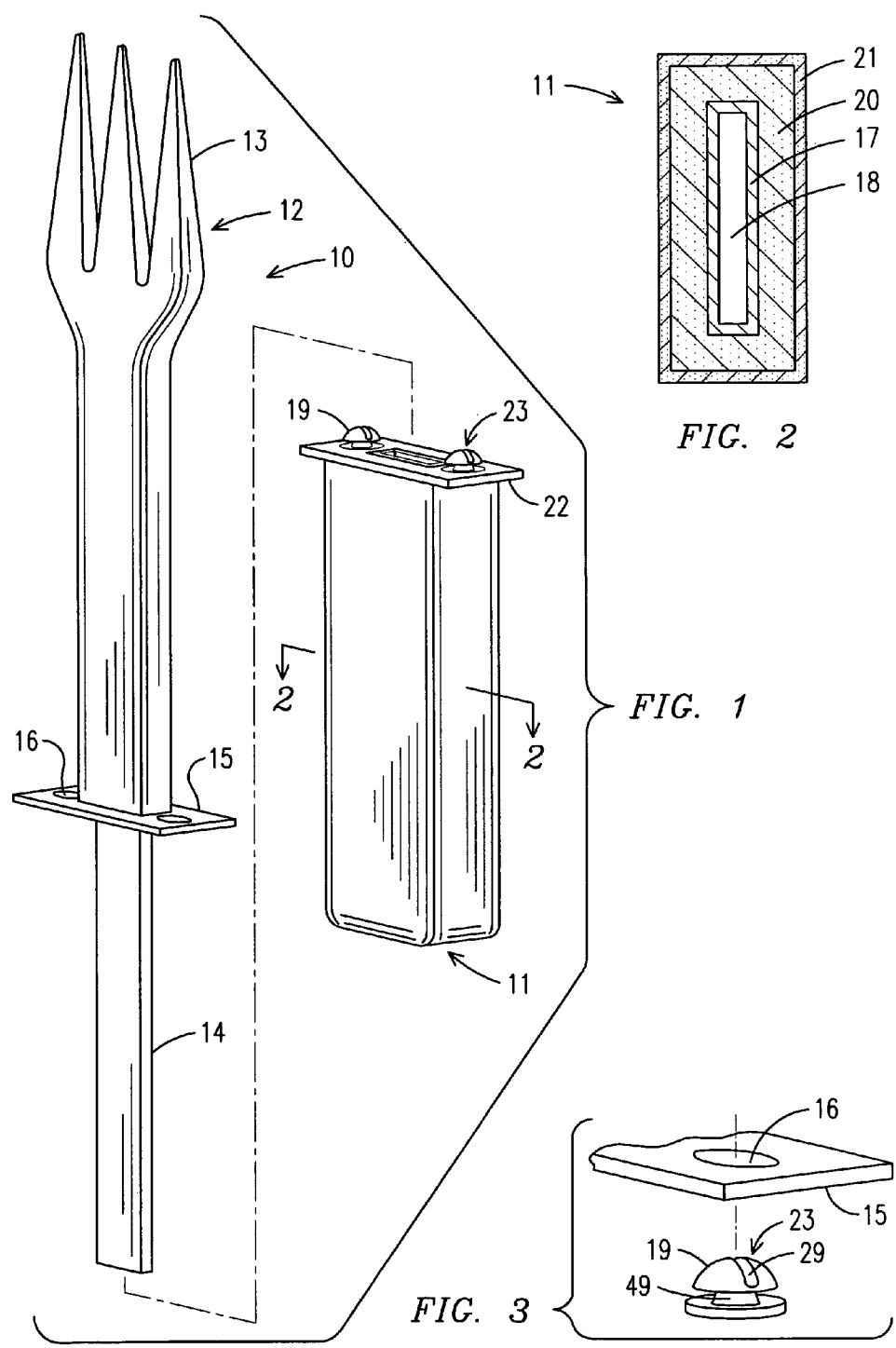
FIG. 1 shows an exploded view of a culinary tool having the present sterilizing handle.
FIG. 2 is a cross-section through the removable handle of FIG. 1.
FIG. 3 is an exploded perspective of the locking mechanism for locking the handle to the culinary tool.

Referring to the drawings, FIGS. 1 through 3, a culinary tool 10 has a removable handle 11. The culinary tool 10 is illustrated as a fork 12 having a plurality of tines 13 and a tang 14 which has a guard 15 which, in this case is a cross-guard. The cross-guard 15 has a pair of openings 16 therethrough. The fork 12 may be made of any material desired but would be typically be made of a metal, such as stainless steel.

The handle 11, as seen in FIG. 2, has a hard casing or sleeve 17 having a passageway 18 sized to slide over the tang 14 of the fork 12. The casing is wrapped and impregnated with an impregnatable foam 20, such as a polystyrene foam, to form a reservoir which is impregnated with a disinfectant, such as alcohol. The impregnatable foam reservoir 20 is wrapped and sealed in a semipermeable membrane 21, such as cellulose acetate film having a large plurality of microscopic openings therein. A semipermeable membrane is one that allows molecules or small particles to pass through it with the rate of passage depending upon the pressure and concentration of the solute disinfectant material within the impregnable foam reservoir 20. The impregnable foam reservoir 20 is completely hermetically enclosed between the film layer 21 on one side and the hard sleeve 18 on the other. The hard sleeve 18 has a flange 22 extending therefrom which has the film layer 21 attached thereto. The flange 22 has a pair of latching knobs 23 thereon positioned for alignment with the openings 16 in the guard 15.

The latching knobs 23, as seen in FIG. 3, may have a non-round shaped knob 19 and may have a standard screwdriver slot 29 thereon. The knob 19 is shaped to fit through the opening 16, as can be seen in FIG. 3 as a non-circular opening. Knob 19 can then be rotated to rotate the latching edges 49 over the edge of the outside of the flange opening 16 to thereby lock the handle 11 to the fork 12 by locking the flange 22 to the cross-guard 15. This latching allows for the quick attachment and removal of the handle 11 so that once the disinfectant solution in the reservoir 20 has been used up, the handle 11 can be quickly removed and replaced with a new handle having a filled reservoir.

In operation, when an individual grabs the fork at a salad bar or the like and applies pressure to the handle 11, small amounts of disinfectant ooze through the permeable film 21 for sterilizing the handle and the person's hands to avoid the spread of bacteria between a plurality of users of the culinary tool fork 12.

Figure 5:
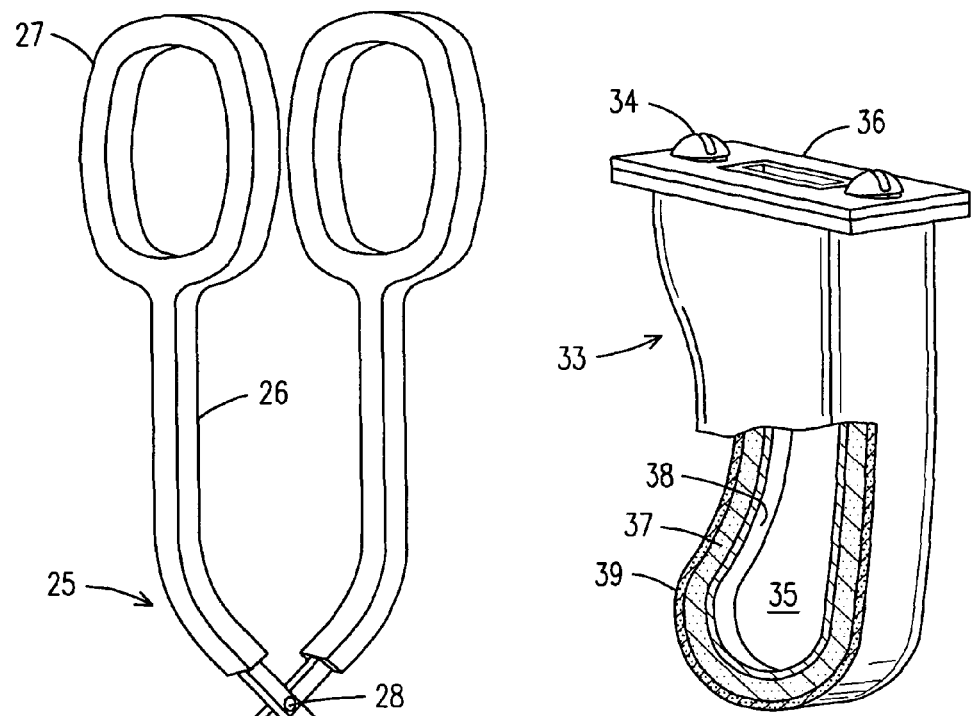
FIG. 5 is a perspective with a partial cut-away of the sterilizing handle for the tongs of FIG. 4.
Figure 4:
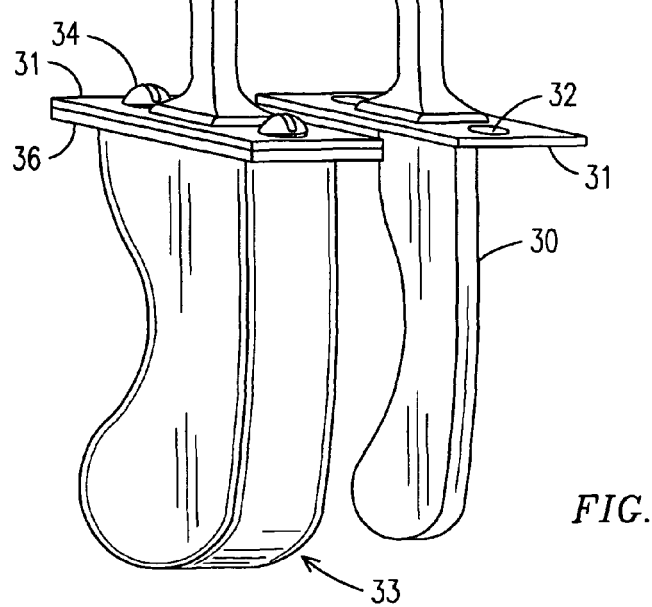
FIG. 4 is a perspective view of a pair of salad tongs having a sterilizing handle on one of the tong tangs.

Turning to FIG. 4, a more common set of tongs 25 has a pair of arms 26, each arm having a gripping jaw 27 on the end thereof, the arms are hinged at 28. Each arm has a tang 30 having a guard 31 having an opening or a pair of openings 32. Each tang has a handle 33 removably attached thereto with the fastening members 34. Each handle member 34, as seen in FIG. 5, has an interior sleeve 38 defining a space 35 as the same shape as the tang 30. The interior casing 38 has a flange 36 on the end thereof having the latching knobs 34 attached thereto for insertion through the openings 32 of the guard 31. The knobs 34 are rotated to removably latch the handle to the tongs in the same manner as illustrated in FIGS. 1 and 3. An impregnable foam reservoir 37 is wrapped around the casing 38 and in turn is hermetically sealed with a semipermeable film layer 39 which is attached to the flange 36 to hermetically seal the reservoir 37 thereinside.

In operation, each handle is placed on the tang 30 of each arm 26 of the tongs 25 and is latched by sliding the non-circular knobs 34 through the openings 32 in the guards 31 and then rotating the knobs 34 to remove and latch the handle 33 to the tangs 30 of the arms 26 of the tongs 25. The reservoir 37 may be saturated with a disinfectant, such as alcohol, or any other disinfectant desired so that when the tongs are grabbed by a patron in a restaurant, pressure is applied to the handles 33. Disinfectant will pass through the semipermeable layer 39 to maintain each handle in a generally sterile condition to protect the hands and the users of subsequent users of the tongs.

It should be clear at this time that a sterilizing handle for a culinary tool, such as a fork, salad tongs, knife or the like, has been provided which advantageously maintains the handle in a sterile condition protecting against the passage of bacteria from one patron using the tool to the next. However, the present invention is not to be considered as limited to the forms shown which are to be considered illustrative rather than restrictive.

I claim:

1. A sterilizing handle for a culinary tool comprising:
a culinary tool having a tang extending therefrom and having a handle guard extending generally perpendicular to said tang; and
a handle removably attached to said culinary tool tang, said handle having a generally nonporous sleeve shaped to fit over said tang and having an open end having a flange extending generally perpendicular therefrom and positioned for attaching said flange to said handle guard, and said handle having a disinfectant impregnated foam reservoir encapsulated in a semipermeable membrane covering said nonporous sleeve;
whereby applying pressure to the culinary tool handle causes disinfectant material to ooze through said semipermeable membrane to disinfect said handle.

2. The sterilizing handle for a culinary tool in accordance with claim 1 in which said handle guard has an opening therethrough for attaching said handle flange thereto.

3. The sterilizing handle for a culinary tool in accordance with claim 2 in which said handle flange has a movable locking member shaped to fit through the opening in said guard in one position and moveable to a second position to attach said handle flange to said guard.

4. The sterilizing handle for a culinary tool in accordance with claim 3 in which said handle guard opening has a generally oval shape.

5. The sterilizing handle for a culinary tool in accordance with claim 4 in which said locking member is generally oval shaped and sized to fit through said handle guard opening and is rotatable to overlap the edges of said handle guard opening.

6. The sterilizing handle for a culinary tool in accordance with claim 3 in which said disinfectant impregnated foam reservoir is a poly styrene foam saturated with a disinfectant solution.

7. The sterilizing handle for a culinary tool in accordance with claim 6 in which said semipermeable membrane is cellulose acetate film having a plurality of microscopic openings therein.

8. The sterilizing handle for a culinary tool in accordance with claim 7 in which said generally nonporous sleeve is a hard polymer hollow sleeve open at one end.

9. The sterilizing handle for a culinary tool in accordance with claim 8 in which said culinary tool is a spoon.

10. The sterilizing handle for a culinary tool in accordance with claim 8 in which said culinary tool is a fork.

11. A process of maintaining a sterile handle for a culinary tool comprising the steps of:
selecting a culinary tool having a tang extending therefrom and having a handle guard extending generally perpendicular to said tang;
selecting a handle shaped to be removably attached to said culinary tool, said handle having a hollow generally nonporous sleeve shaped to fit over said selected culinary tool tang and having an open end having a flange extending generally perpendicular therefrom and positioned for attaching said flange to said handle guard, said handle having a disinfectant impregnated foam reservoir encapsulated in a semipermeable membrane covering said nonporous sleeve;

sliding said handle over said selected culinary tool tang; and removably attaching said handle flange to said culinary tool guard;

whereby applying pressure to said culinary tool handle causes disinfectant material to ooze through said semi-permeable membrane to disinfect the handle.

* * * * *